United States Patent [19]
Estes et al.

[11] 3,985,678
[45] Oct. 12, 1976

[54] ISOPARAFFIN ALKYLATION

[75] Inventors: John H. Estes, Wappingers Falls; Edward L. Cole, Fishkill, both of N.Y.

[73] Assignee: Texaco Inc., New York, N.Y.

[22] Filed: Mar. 14, 1975

[21] Appl. No.: 558,391

Related U.S. Application Data

[60] Continuation-in-part of Ser. No. 484,095, June 28, 1974, abandoned, which is a division of Ser. No. 343,322, March 21, 1973, Pat. No. 3,867,475.

[52] U.S. Cl. ........................... 252/429 R; 252/428; 252/436
[51] Int. Cl.² ......................................... B01J 27/02
[58] Field of Search ................. 260/683.63, 683.51, 260/683.59, 683.58; 252/428, 429 R, 436

[56] References Cited
UNITED STATES PATENTS

| | | | |
|---|---|---|---|
| 3,531,546 | 9/1970 | Hervert | 260/683.51 |
| 3,678,120 | 7/1972 | Bloch | 252/436 X |

OTHER PUBLICATIONS

Mellor, *A Comprehensive Treatise on Inorganic & Theoretical Chemistry*, vol. 6, p. 53, (1925).

*Primary Examiner*—Patrick P. Garvin
*Attorney, Agent, or Firm*—T. H. Whaley; C. G. Ries; Douglas H. May, Jr.

[57] ABSTRACT

A strong acid catalyzed alkylation process wherein an isoparaffin is alkylated with an alkylating agent such as olefin hydrocarbon and alkyl sulfates, in the liquid phase, at a superatmospheric pressure and a temperature in the range of from below zero to about 100°F, employing a liquid catalyst consisting essentially of about 98.5 to about 88 weight percent of an acid selected from $H_2SO_4$, $HFSO_3$, and mixtures thereof, about 0.5 to about 8 weight percent acid oils, about 0 to about 6 weight percent water, and having at least about 0.1 weight percent carbon dioxide dissolved therein.

9 Claims, No Drawings

ISOPARAFFIN ALKYLATION

This application is a continuation-in-part of application Ser. No. 484,045, filed June 28, 1974, now abandoned, which in turn is a divisional application of application Ser. No. 343,322, filed Mar. 21, 1973, now issued as U.S. Pat. No. 3,867,475.

BACKGROUND OF THE INVENTION

The present invention relates to alkylation of isoparaffin hydrocarbons with alkylating agents in the presence of a strong acid catalyst. Particularly, the invention relates to production of $C_7 - C_8$ hydrocarbons, suitable for use as motor fuel, by alkylation of isoparaffin hydrocarbon with olefins. More particularly, this invention relates to an isobutane-butylene alkylation process catalyzed by an acid catalyst comprising sulfuric acid and/or flurosulfonic acid containing dissolved carbon dioxide, having high selectivity for production of trimethyl pentanes.

Processes for acid catalyzed alkylation wherein an isoparaffin is reacted with an alkylating agent such as an olefin, alcohol, alkyl sulfate, etc., to form alkyl hydrocarbons are well known. Such alkylation reactions are generally carried out in the liquid phase at temperatures in the range of about 0° – 100° F. and at pressures sufficient to maintain reactants in the liquid phase. Of particular importance is alkylation of isobutane with butylene to form octane hydrocarbons, especially trimethyl pentanes, which are useful as components of motor fuel. The butylenes which may be a mixture of normal and isobutylenes are reacted with a molar excess of isobutane in the liquid phase in the presence of a strong acid such as sulfuric acid, flurosulfonic acid, and mixtures thereof, at temperatures of 0° F. to 100° F. and pressures of 10 to 150 psig, or higher.

The discussion herein is presented with respect to formation of octane hydrocarbons, however, it is to be understood that the discussion is equally applicable to alkylation reactions generally, and particularly to alkylation of isobutane and isopentane with lower molecular weight olefins such as propylene, butylenes, and pentalenes. Basically, it is desirable in an alkylation reaction to promote formation of the 1:1 olefin-paraffin adduct; that is, formation of trimethyl pentanes from butylenes and isobutane.

In strong acid catalyzed alkylation reactions, side reactions occur in which $C_{12}^+$ products are formed as well as the desirable trimethyl pentanes. A portion of $C_{12}^+$ products then undergo cracking to form undesirable lighter hydrocarbons, such as for example, $C_5$, $C_6$, and $C_7$ light alkylate hydrocarbons. The result of such side reactions, then, is to reduce production of the desired $C_8$ products and to lower the octane number of the alkylate product obtained.

SUMMARY OF THE INVENTION

Now, according to the present invention, novel acid alkylation catalysts are disclosed for use in alkylation processes wherein gasoline boiling range alkylate hydrocarbons are produced by alkylation of $C_4 - C_5$ isoparaffin hydrocarbons with $C_3 - C_5$ olefins, or olefinacting alkylating agents such as alcohols, alkyl sulfates, etc. Preferably, the acid catalysts of the present invention are used in alkylation processes wherein olefin hydrocarbon is reacted with a molar excess of isoparaffin hydrocarbon at temperatures of from about 0° – 100° F., pressures of about 10–150 psig and higher, for production of alkylate hydrocarbons useful as gasoline blending components.

The alkylation catalysts of the present invention comprises about 98.5 – 88 weight percent of an acid selected from $H_2SO_4$, $HFSO_3$, and mixtures thereof, about 0.5 – 8 weight percent acid oils, and containing carbon dioxide gas dissolved therein. Preferably, the catalysts of the present invention are saturated with $CO_2$ at the temperature, pressure, and concentration of reactants and catalysts existing in alkylation processes within which such catalyst is employed. Catalysts of the present invention may contain about 0–6 weight percent water.

By employing the carbon dioxide containing acid catalyst of the present invention in an alkylation process, formation of desirable 1:1 olefin-isoparaffin adduct is increased over that obtained from an alkylation process wherein strong acid catalysts of the prior art are employed. Additionally, formation of undesirable, low octane number light alkylate and heavy alkylate hydrocarbons is decreased. In an alkylation process employing the carbon dioxide containing acid catalyst of the present invention, wherein isobutane is alkylated with butylenes, octane hydrocarbons are the major product of the process. Also, the major portion of the octane hydrocarbons is trimethyl pentanes which have high octane numbers and are particularly desirable as components for gasoline blending. Reduction of light alkylate components and $C_9^+$ heavy alkylate components, by using catalysts of the present invention, improves volatility characteristics of the alkylate product. These, and other advantages will be more fully set out in the detailed description of the invention which follows.

DETAILED DESCRIPTION OF THE INVENTION

Unexpectedly, accordingly to the present invention, we have discovered that solution of carbon dioxide gas into liquid alkylation acid catalysts comprising $H_2SO_4$, $HFSO_3$ and mixtures thereof improves subsequent alkylation reactions by increasing the yield of desirable 1:1 isoparaffin-olefin adducts, particularly the desirable highly branched isomers. The reasons for such improvement are not presently known. It may be speculated that solution of carbon dioxide into the acid catalyst reduces the acid viscosity such that better mixing of hydrocarbon reactant and catalyst is obtained, or that hydrocarbon solubility in the acid catalyst is increased. However, such speculations are unsupported and are not to be taken as limitations upon the present invention.

Carbon dioxide treatment according to the method of the present invention is applicable to alkylation catalysts containing strong Bronsted acids. The strong Bronsted acids are those which readily give up a proton, and include HF as well as $H_2SO_4$, $H_2SO_4 - SO_3$, $H_2SO_4 - HSO_3F$, $H_2SO_4 - HSO_3Cl$, and $H_2SO_4-HB(HSO_4)_4$. Such acids are employed in catalysts used in the ($C_4$ to $C_{10}$) isoparaffin — ($C_3$ to $C_{10}$) olefin alkylation reactions. Particularly, carbon dioxide treatment improves selectivity of catalysts containing sulfuric acid, flurosulfonic acid, and mixtures thereof for formation of desirable 1:1 isoparaffin-olefin adducts in an alkylation reaction. Especially, carbon dioxide treated sulfuric acid catalyst has improved selectivity for production of trimethyl pentanes in an alkylation reaction employing isobutane and butylene reactants.

Alkylation reactions, as exemplified by strong acid catalyzed reaction of butylenes and isobutane to form octane, are characterized by the problem that the formation of the 1:1 olefin-paraffin adduct, e.g., octane, at the start of the reaction, when fresh acid is employed as catalyst, does not proceed at a desirable rate. Thus, reactant hydrocarbons during the initial period of the reaction participate in undesirable side reactions at a much faster rate than the desirable but slower reaction to form the stable 1:1 olefin-paraffin adduct, e.g., octane. These side reactions lead to the formation of $C_{12}^+$ products which then undergo cracking reactions to form undesirable lighter hydrocarbons such as, for example, $C_5$, $C_6$, and $C_7$ light alkylate components as well as $C_9^+$ heavy alkylate hydrocarbons. Such heavy and light alkylate hydrocarbons have relatively low octane numbers. This predominance of undesirable side reactions generally continues for a period of time, at the end of which period there is a marked change in the selectivity of the alkylation reaction to formation of the 1:1 adduct.

During this period, commonly referred to as the "induction period", acid oils are being formed and are accummulating in the acid catalyst. These acid oils are complex high molecular weight reaction products of hydrocarbon and strong acid from the catalyst, the chemical nature of which is incompletely understood. When the concentration of acid oils reaches a significant level in the acid catalyst, a change in the selectivity of reactions occurs and formation of the desirable 1:1 olefin-isoparaffin adduct becomes predominant over competing side reactions. The time of this induction period will vary with the hydrocarbon reactants and catalyst used in the alkylation reaction, but generally lasts about 200 hours when $HFSO_3$ is employed as catalyst and about 50 hours when $H_2SO_4$ is employed as catalyst.

For continuous alkylation processes, wherein catalyst is recycled for contact with additional hydrocarbon reactants, the induction period is not a substantial problem. The recycled catalyst contains appreciable amounts of the acid oils, and the alkylation reaction for forming the desirable 1:1 olefin-isoparaffin adduct predominates over competing side reactions. The acid oils comprise about 0.5 – 8 weight percent of the catalysts in such reactions. At concentrations below about 0.5 weight percent the concentration of acid oils may be insufficient to provide the full advantage for the desired alkylation reaction. At concentrations above about 8 weight percent, the acid oils dilute the strong acid in the catalyst and may cause formation of hydrocarbon-acid emulsions which will not separate rapidly, thus encouraging undesirable olefin polymerization reactions.

The induction period may be substantially eliminated for batch alkylation reactions and for continuous alkylation reactions starting-up with fresh acid as catalyst by addition to the fresh acid of a minor amount of spent catalyst, containing acid oils, from a previous alkylation reaction.

Generally, alkylation catalysts comprising $H_2SO_4$, $HFSO_3$, and mixtures thereof, contain some amount of water which comes from the fresh acid, the reactant hydrocarbons, or as a by-product of side reactions involving the acid catalyst. As the water concentration increases, the acid concentration in the catalyst is diluted and olefin polymerization reactions increase. Thus, it is desirable to maintain the water concentration at about 0–6 weight percent of the catalyst.

Such alkylation catalysts, comprising $H_2SO_4$, $HFSO_3$, and mixtures thereof preferably comprise about 98.5 – 88 weight percent acid. At acid concentrations above about 98.5 weight percent, the catalyst may require substantial time as an induction period before the desired reactions for formation of 1:1 olefin-isoparaffin adduct begin to predominate. At acid concentrations below about 88 weight percent, olefin polymerization reactions begin to increase substantially resulting in lower quality alkylate product. Thus, liquid alkylation catalysts contemplated for use in the present invention comprise about 98.5 – 88 weight percent of an acid selected from $H_2SO_4$, $HFSO_3$, and mixtures thereof, about 0.5 – 8 weight percent acid oils, and about 0–6 weight percent water. Such liquid alkylation catalysts may be maintained within the desired composition range in continuous alkylation processes by periodically or continuously withdrawing a minor portion of spent catalyst from the process and replacing it with fresh concentrated acid, preferably comprising about 99.5 – 98 weight percent acid.

According to the present invention, liquid alkylation catalysts, as described above, are treated with carbon dioxide gas under conditions to dissolve carbon dioxide into the liquid catalyst. Preferably, liquid acid and gaseous carbon dioxide are contacted under conditions of intimate mixing at superatmospheric pressures and temperatures in the range of below zero to 100° F. More preferably, pressures in the range of about 50–100 psig and temperatures in the range of 20°–75°F. are employed. Higher pressures and lower temperatures favor solution of carbon dioxide in the liquid strong acid. Pressures of at least 50 psig are preferred. Pressures greater than about 1000 psig do not offer any substantial economic advantage. Lower temperatures favor solution of carbon dioxide in liquid strong acid catalyst. At temperatures below about 20° F., liquid viscosity increases substantially and extra refrigeration must be provided. Temperatures in the range of about 20°–60° F. are within the usual temperature range of the alkylation reactions contemplated herein, thus extra refrigeration to cool the liquid strong acid is not required.

Benefits of the present invention are obtained by dissolving carbon dioxide into the liquid strong acid catalyst. Maximum benefits are obtained when the liquid strong acid catalyst is saturated with carbon dioxide at the alkylation reaction conditions employed. Preferably dissolved carbon dioxide is present in a weight ratio of at least 0.1 part carbon dioxide per 100 parts liquid strong acid, although lower concentrations of carbon dioxide will confer some benefit to the catalyst.

In order to encourage solution of carbon dioxide in strong acid it is usually desirable to employ an excess of carbon dioxide. In treating the strong acid, for solution of carbon dioxide therein, weight ratios of carbon dioxide to strong acid of about 0.1/100 and higher may be employed. Preferably weight ratios of carbon dioxide to strong acid of at least 3/100 are employed. Great excesses of carbon dioxide to strong acid in the acid treatment are not necessary, and excess carbon dioxide which does not dissolve in treated strong acid may be recovered for treatment of additional acid.

Intimate mixing of carbon dioxide gas with liquid strong acid may be accomplished by any effective gas-liquid contact means such as asperation, sparging, agitation, etc. In a preferred mode of operation, carbon dioxide and liquid strong acid are contacted before employing the treated strong acid as catalyst in an alkylation reaction. In processes wherein alkylation acid is recycled from an acid settler to an alkylation reaction zone, the recycle acid may be conveniently treated with carbon dioxide in a separate treating zone prior to introduction into the alkylation reaction zone. However, if desired, the carbon dioxide may be introduced directly into the alkylation reaction zone with the mixing means provided to ensure contact of acid catalyst with hydrocarbon reactants also being used to contact the liquid strong acid with the carbon dioxide.

Contact time of carbon dioxide with strong acid being treated need only be sufficient to effect solution of the desired amount of carbon dioxide into the strong acid. Contact times of from a few seconds to 24 hours and longer may be employed. Necessary contact time will be shorter with better mixing and more intimate contact of carbon dioxide with the strong acid. Preferred contact times for any particular acid treating system may be easily established by observing the rate of solution of carbon dioxide into the strong acid under the conditions of pressure, temperature and degree of mixing present in the particular system under consideration.

Conventional strong acid catalyzed alkylation reactions may be carried out employing the improved process of the present invention. Thus, the alkylation process can comprise reaction of an isoparaffin with an olefin or other alkylating agent. In alkylation reactions catalyzed by sulfuric acid and flurosulfonic-sulfuric acid mixtures, alkylsulfates, such as diisopropylsulfate, diisobutylsulfate, etc., may replace the corresponding olefin in whole or in part as alkylating agent.

The alkylation reactions contemplated in the present invention are carried out in the liquid phase. However, the reactants need not be normally liquid hydrocarbons. Alkylation reaction conditions can vary in temperature from below zero to about 100° F., and can be carried out at pressures of from atmospheric to 1000 psig and higher. For continuous processes, olefin space velocities of from about 0.01 to about 20 volumes olefin/hour/volume of catalyst may be employed. Molar ratios of isoparaffin hydrocarbon to alkylating agent of from about 1:1 to about 50:1 and higher may be employed. Preferably, substantial molar excess of isoparaffin to olefin is maintained in alkylation reactions, with molar ratios of isoparaffin to olefin of from about 5:1 to about 20:1 being particularly preferred.

Carbon dioxide treated acid catalysts comprising sulfuric acid, flurosulfonic acid and mixtures thereof can be employed in the alkylation reactions. However, sulfuric acid and mixtures comprising sulfuric acid and flurosulfonic acid in weight ratios of about 10/1 to about 5/1 are preferred. In the process of the present invention, where a carbon dioxide treated strong acid catalyst is employed, the preferred temperatures for use of sulfuric acid containing catalysts are between 30° and 75° F. and preferred pressures are 50 psig to 150 psig and higher. When using flurosulfonic acid or mixtures of sulfuric and flurosulfonic acid in the catalyst, preferred temperatures are between 0° F. and 75° F. and preferred pressures are 50 psig to 150 psig and higher.

The following examples are offered to illustrate the improvement of the present invention.

EXAMPLE I

To demonstrate the present invention, 300 ml. of 94.43 weight percent sulfuric acid, containing 30 ml. of acid from a previous alkylation run was charged to a reactor equipped with cooling coils and a stirrer. The autoclave was pressured to 100 psig with $CO_2$ and the acid was stirred at about 50° F. for 15 minutes. Upon completion of the stirring, the autoclave was depressured to 50 psig and 77 grams of hydrocarbon comprising isobutane and butene-2 in a liquid volume ratio of 6.25/1 respectively was charged to the reactor. Under alkylation conditions including a temperature of 50° F., a pressure of about 105 psig and constant stirring, the acid-hydrocarbon mixture was allowed to react for 15 minutes. At the end of the reaction time the stirring was stopped and the reaction mixture was separated into an acid phase and a hydrocarbon phase.

In a second run, for comparative results, the experiment above was repeated at the same operating conditions, except nitrogen was substituted for carbon dioxide in the acid treating step prior to the alkylation reaction. The nitrogen was employed to maintain the 105 psig operating pressure in the second run.

The hydrocarbon phase from each run above was separately fractionated to recover pentane and heavier alkylate therefrom, and the recovered alkylate fractions were subjected to analysis. Results of such analyses are reported in Table I below.

TABLE I

| Treating Gas | $CO_2$ | $N_2$ |
|---|---|---|
| Alkylate yield, basis olefin consumed (wt.%) | 158.0 | 185.0 |
| Alkylate Composition (Vol. %) | | |
| $C_5$ | 2.3 | 3.6 |
| $C_6$ | 4.8 | 5.6 |
| $C_7$ | 4.7 | 5.7 |
| $C_8$ | 56.4 | 53.6 |
| $C_9^+$ | 31.9 | 31.4 |
| Alkylate Bromine No. | 2.6 | 3.8 |
| $C_8$ Distribution (Vol. % of Alkylate) | | |
| Trimethyl pentane | 43.1 | 36.9 |
| Dimethyl hexane | 3.0 | 3.6 |
| Unidentified $C_8$ | 10.3 | 13.1 |

From the Table I it can readily be seen that the alkylation reaction employing the carbon dioxide containing catalyst of the present invention was more selective for production of desirable $C_8$ range alkylate, and particularly for production of desirable trimethyl pentanes, than was the alkylation reaction employing nitrogen treated sulfuric acid catalyst. Additionally, the bromine number, indicating degree of unsaturation, was lower for alkylate produced in the reaction using the carbon dioxide containing acid catalyst.

EXAMPLE II

In the same reactor system employed in Example I, additional alkylation reactions were performed to show the advantage of using the carbon dioxide containing catalysts of the present invention, as compared to alkylation reactions using sulfuric acid alkylation catalyst without $CO_2$ contained therein. Summaries of operating conditions and analytical results for these alkylation runs are shown in Table II below.

TABLE II

| Run Number | 1 | 2 | 3 | 4 | 5 | 6 | 7 |
|---|---|---|---|---|---|---|---|
| Acid (Ml) | 100.0 | 100.0 | 100.0 | 100.0 | 100.0 | 100.0 | 100.0 |
| H2SO4 (wt. % in acid) | 94.6 | 96.13 | 96.13 | 96.1 | 94.6 | 96.13 | 94.6 |
| $CO_2$ treating pressure (psig) | 600.0 | 75.00 | 80.00 | 85.00 | — | — | — |
| $CO_2$ wt. % of Acid | — | 0.3 | 0.6 | 0.8 | 0 | 0 | 0 |
| Hydrocarbon Charge (gms) | 78 | 72 | 78 | 75 | 78 | 76 | 76 |
| Isobutane/butene-2 ratio | 6.4/1 | 6.6/1 | 6.6/1 | 6.6/1 | 6.4/1 | 6.6/1 | 6.6/1 |
| Alkylation temperature (°F.) | 47–50 | 50 | 50 | 50 | 50 | 50 | 50 |
| Alkylation pressure (psig) | 95 | 75 | 80 | 85 | 45 | 60 | 55 |
| Alkylation reaction time (min) | 15 | 15 | 15 | 15 | 15 | 15 | 15 |
| Alkylate recovery, pentane and heavier (gms) | 20.4 | 17.5 | 19.6 | 21.3 | 14.9 | 15.5 | 19.4 |
| Alkylate yield (wt. % olefin) | 192 | 195 | 190 | 205 | 142 | 149 | 170 |
| Alkylate composition | | | | | | | |
| $C_5$ | 2.1 | 2.5 | 2.5 | 2.0 | 1.4 | 2.7 | 3.0 |
| $C_6$ | 4.3 | 5.0 | 5.0 | 4.8 | 3.3 | 5.6 | 5.6 |
| $C_7$ | 4.3 | 4.9 | 4.8 | 4.9 | 4.0 | 5.8 | 5.5 |
| $C_8$ | 72.3 | 61.9 | 62.6 | 60.4 | 60.6 | 63.1 | 59.0 |
| $C_9^+$ | 17.0 | 25.6 | 25.1 | 27.9 | 30.7 | 22.6 | 26.7 |
| Alkylate Bromine Number | 1.7 | 3.0 | 3.4 | 4.2 | 5.4 | 3.0 | 4.6 |
| C8 fraction composition (Vol. % of Alkylate) | | | | | | | |
| Trimethyl pentane | 58.0 | 49.2 | 50.9 | 47.0 | 42.8 | 46.2 | 43.3 |
| Dimethyl hexane | 4.7 | 3.2 | — | 3.8 | 4.4 | 4.9 | 4.6 |
| Unidentified $C_8$ | 9.6 | 10.5 | 11.7 | 9.8 | 13.3 | 12.0 | 11.1 |

Runs 1 through 4 were made employing carbon dioxide containing sulfuric acid alkylation catalyst. The sulfuric acid catalyst, prior to carbon dioxide treatment, comprised fresh 98.5% $H_2SO_4$ mixed with spent catalyst containing acid oils. In Run 1, acid catalyst was mixed with carbon dioxide at 600 psig and 50° F. for 48 hours. At the end of this time, pressure was reduced and the alkylation reaction was performed at 95 psig. In Runs 2–4, carbon dioxide was added to the acid catalyst in the reaction vessel, in the weight fractions shown, and the alkylation reactions were performed at the resulting pressures. For Runs 5–7, no carbon dioxide was dissolved in the sulfuric acid catalyst.

From an examination of the results obtained in this example, alkylation runs employing carbon dioxide containing sulfuric acid catalyst produce greater yields of alkylate, as a weight percent of olefin consumed in the reaction, than alkylation runs employing untreated acid catalyst. Also, alkylate from Runs 1–4 contains greater amounts of $C_8$ hydrocarbons, particularly the desirable trimethyl pentane isomers. As indicated by the Bromine number, olefin content of alkylate produced with carbon dioxide containing catalyst is lower than for alkylate produced with catalyst free of carbon dioxide.

From the foregoing discussion and examples, the advantages of the improvement of the present invention can readily be seen. By employing the novel alkylation catalysts comprising about 98.5 – 88 weight percent acid selected from sulfuric, flurosulfonic and mixtures, about 0.5 – 8 weight percent acid oils, about 0 – 6 weight percent water, and containing carbon dioxide dissolved therein, in the alkylation of lower molecular weight isoparaffin hydrocarbons with olefins having three to five carbon atoms, alkylate of improved quality can readily be obtained.

Obviously, many modifications and variations of the invention, as hereinabove set forth, may be made without departing from the spirit and scope thereof. Therefore, only such limitations should be imposed as are indicated in the appended claims.

We claim:

1. A catalyst for use in an alkylation process wherein an isoparaffin hydrocarbon is alkylated with an olefin-acting alkylating agent; which catalyst consists essentially of about 98.5 to about 88 weight percent of a liquid acid selected from sulfuric, fluorosulfonic, and mixtures thereof, about 0.5 to about 8 weight percent acid oils, about 0 to about 6 weight percent water, and having at least about 0.1 parts by weight carbon dioxide gas per 100 parts liquid acid dissolved therein.

2. The catalyst of claim 1 containing the saturation amount of carbon dioxide, determined at the operating conditions of said alkylation process.

3. The catalyst of claim 1 wherein the liquid acid is sulfuric acid.

4. The catalyst of claim 1 wherein the liquid acid is a mixture of sulfuric acid and flurosulfonic acid in a weight ratio of about 10/1 to about 5/1, respectively.

5. An alkylation catalyst, for use in a process wherein isoparaffin hydrocarbon is alkylated with an olefin-acting alkylating agent, consisting essentially of about 98.5 to about 88 weight percent of a liquid acid selected from sulfuric, fluorosulfonic, and mixtures thereof, about 0.5 to about 8 weight percent acid oils, and at least about 0.1 part by weight carbon dioxide per 100 parts liquid acid.

6. The catalyst of claim 5 containing the saturation amount of carbon dioxide.

7. The catalyst of claim 6 containing not more than about 6 weight percent water.

8. The catalyst of claim 7 wherein the liquid acid is sulfuric acid.

9. The catalyst of claim 7 wherein the liquid acid is a mixture of sulfuric acid and flurosulfonic acid in a weight ratio of from about 10/1 to about 5/1 respectively.

* * * * *